(12) United States Patent
Akasapu et al.

(10) Patent No.: US 10,653,646 B2
(45) Date of Patent: May 19, 2020

(54) EPINEPHRINE COMPOSITIONS AND CONTAINERS

(71) Applicant: Nevakar Inc., Bridgewater, NJ (US)

(72) Inventors: Prem Sagar Akasapu, Edison, NJ (US); Kumaresh Soppimath, Skillman, NJ (US); Reema Ajitkumar Puri, Hillsborough, NJ (US); Iouri V. Ilitchev, Hillsborough, NJ (US); Milan Patel, Edison, NJ (US); Pooja H. Tendulkar, East Brunswick, NJ (US)

(73) Assignee: Nevakar Inc., Bridgewater, NJ (US)

( * ) Notice: Subject to any disclaimer, the term of this patent is extended or adjusted under 35 U.S.C. 154(b) by 0 days.

(21) Appl. No.: 16/360,995

(22) Filed: Mar. 21, 2019

(65) Prior Publication Data

US 2019/0290602 A1    Sep. 26, 2019

Related U.S. Application Data

(60) Provisional application No. 62/647,303, filed on Mar. 23, 2018.

(51) Int. Cl.
| | | |
|---|---|---|
| *A61K 31/137* | (2006.01) | |
| *A61K 9/00* | (2006.01) | |
| *A61K 9/08* | (2006.01) | |

(52) U.S. Cl.
CPC .......... *A61K 31/137* (2013.01); *A61K 9/0019* (2013.01); *A61K 9/08* (2013.01)

(58) Field of Classification Search
CPC ....... A61K 31/137; A61K 9/0019; A61K 9/08
See application file for complete search history.

(56) References Cited

U.S. PATENT DOCUMENTS

| | | | |
|---|---|---|---|
| 3,966,905 A | 6/1976 | Nite | |
| 6,111,639 A * | 8/2000 | Reduto | G01J 3/02 356/300 |
| 9,119,876 B1 | 9/2015 | Kannan et al. | |
| 9,789,071 B2 | 10/2017 | Fleming | |
| 2004/0076588 A1 | 4/2004 | Batycky et al. | |
| 2012/0029085 A1 | 2/2012 | MacKay | |
| 2015/0119440 A1 | 4/2015 | Karolchyk et al. | |
| 2015/0374832 A1 | 12/2015 | Surakitbanharn | |
| 2016/0058715 A1 | 3/2016 | Rakesh et al. | |
| 2017/0088333 A1 | 3/2017 | Devouassoux et al. | |
| 2017/0165206 A1 | 6/2017 | Kannan et al. | |
| 2017/0189352 A1 * | 7/2017 | Sanghvi | A61K 31/137 |
| 2018/0028671 A1 | 2/2018 | Surakitbanharn | |
| 2018/0214394 A1 * | 8/2018 | Puri | A61K 31/137 |

FOREIGN PATENT DOCUMENTS

| | | |
|---|---|---|
| EP | 2 437 781 B1 | 7/2013 |
| FR | 2 779 061 A1 | 12/1999 |
| WO | 93/20168 A1 | 10/1993 |
| WO | 94/08602 A1 | 4/1994 |
| WO | 98/20869 A2 | 5/1998 |
| WO | 00/74772 A1 | 12/2000 |
| WO | 2010/139751 A2 | 12/2010 |
| WO | 2011109340 A1 | 9/2011 |
| WO | 2012/094283 A2 | 7/2012 |
| WO | 2014/057365 A1 | 4/2014 |
| WO | 2014/127015 A1 | 8/2014 |
| WO | 2014/140095 A1 | 9/2014 |
| WO | 2014/202088 A1 | 12/2014 |
| WO | 2016/149028 A2 | 9/2016 |

OTHER PUBLICATIONS

CAS Registry, L- or R-epinephrine, Nov. 1984, CAS, Abstract (Year: 1984).*
Excerpt from US FDA Jan. to Jun. 2019 outsourcing facility product report; 1 pg.
Excerpt from US FDA Jul. to Dec. 2018 outsourcing facility product report; 1 pg.
Connors et al., "Chemical Stability of Pharmaceuticals", A Wiley-Interscience Publication, 1986, 12 pages.
Hoellein et al., "Ficts and facts epinephrine and norepinephrine stability in injectable solutions", International journal of Pharmaceutics, vol. 434, 2012, pp. 468-480.
"Adrenalin (epinephrine injection) 1 mgmL (11000) for intramuscular, subcutaneous, and intraocular use", 2012, pp. 1-10.
Akers, Michael j., "Excipient—Drug Interactions in Parenteral Formulations", Journal of Pharmaceutical Sciences, vol. 91, No. 11, 2002, pp. 2283-2300.
Allen Loyd V., "The Art, Science, and Technology of Pharmaceutical Compounding, fourth edition", American Pharmacists Association, 2012, 29 pages.
Asada et al., "Reactivity of Thiols with Superoxide Radicals", Agricultural and Biological Chemistry, vol. 40, No. 9, 1976, 3 pages.
Baquet et al., "Injectable Formulations of Poorly Water-Soluble Drugs", Springer, AAPS Advances in the Pharmaceutical Sciences, 2012, pp. 209-242.
Corbett et al., "Intraocular adrenaline maintains mydriasis during cataract surgery", British Journal of Opthalmology, vol. 78, 1994, pp. 95-98.
Grubstein et al., "Stabilization of epinephrine in a local anesthetic injectable solution using reduced levels of sodium metabisulfite and edta", Drug Development and Industrial Pharmacy, vol. 18, No. 14, 1992, pp. 1549-1566.
Higuchi et al., "Kinetics and Mechanism of Formation of Sulfonate from Epinephrine and Bisulfite", Journal of the American Chemical Society, vol. 82, Sep. 10, 2019, pp. 1904-1907.
"Physicians' Desk Reference", PDR 62 edition, 2008, 3 pages.
Pramanick et al., "Excipient Selection in Parenteral Formulation Development", Pharma Times, vol. 45, No. 3, 2013, pp. 65-77.
Roscoe et al., "Chelating Agents as Color Stabilizers for Epinephrine Hydrochloride Solutions", Journal of the American Pharmaceutical Association, vol. 45, No. 7, 1956, pp. 464-470.

(Continued)

*Primary Examiner* — Sarah Pihonak
(74) *Attorney, Agent, or Firm* — Umberg Zipser LLP

(57) ABSTRACT

The inventive subject matter provides ready-to-administer, preferably anti-oxidant free, epinephrine compositions with improved stability, and methods for preparing the same. Contemplated compositions can be packaged using blow-fill-seal technology or packaged into flexible IV bags and maintain degradation of the epinephrine at a level of less than 5 wt % when stored over at least one months at between 2-40° C.

20 Claims, No Drawings

(56) References Cited

OTHER PUBLICATIONS

Schroeter et al., "A kinetic study of acid-catalyzed racemization of epinephrine", Scientific edition, 1958, pp. 426-430.
Stepensky et al., "Long-term stability study of L-adrenaline injections: Kinetics of sulfonation and racemization pathways of drug degradation", Journal of Pharmaceutical Sciences, vol. 93, No. 4, 2004, pp. 969-980.
"Chapter 17: Acid-Base Equilibria and Solubility Equilibria", 2011, pp. 1-28.
U.S. Appl. No. 14/658,002 "Epinephrine Formulations and Method of Use" as filed, Mar. 13, 2015, 52 pages.

* cited by examiner

EPINEPHRINE COMPOSITIONS AND CONTAINERS

This application claims priority to US provisional application with the Ser. No. 62/647,303, which was filed Mar. 23, 2018.

FIELD OF THE INVENTION

Background of the Invention

The background description includes information that may be useful in understanding the present invention. It is not an admission that any of the information provided herein is prior art or relevant to the presently claimed invention, or that any publication specifically or implicitly referenced is prior art.

Epinephrine is an endogenous adrenergic neurotransmitter secreted by the medulla of the adrenal glands and acts on both alpha and beta adrenergic receptors found ubiquitously throughout much of the human body. As such epinephrine is involved in various regulatory processes, including regulation of heart beat, blood pressure, airway resistance, and energy metabolism.

Epinephrine, USP is a sympathomimetic catecholamine (adrenergic agent) designated chemically as 4-[1-hydroxy-2(methylamino)ethyl]-1,2-benzenediol, a white, microcrystalline powder and has the following structural formula:

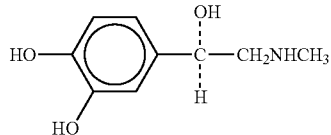

Currently, epinephrine is marketed as a concentrated form for injection (1 mg/mL), which must be diluted with a proper diluent such as dextrose or dextrose/NaCl. Unfortunately, all or almost all of the known diluted epinephrine formulations that are commercially available lack storage stability. Indeed generally, diluted epinephrine solutions must be discarded within one day after reconstitution when stored at room temperature. Since diluted epinephrine solutions are unstable with limited shelf life, such solutions are almost never sold or shipped, but must be prepared at hospitals or doctor's offices for immediate use. Consequently, currently known concentrated epinephrine forms carry a substantial risk of dilution errors, while diluted forms carry a risk of microbial contamination and often have very limited shelf-life due to reduced chemical stability.

Epinephrine in aqueous solution deteriorates rapidly on exposure to air or light (typically via auto-oxidation), turning pink from oxidation to adrenochrome and turning brown from formation of melanin. The rate of this reaction increases with increased pH, increased temperature, and in the presence of metal ions such as aluminum from various rubbers and iron from amber glass ware. Epinephrine solutions may also lose potency as a result of racemization from the biologically active R-isomer to the biologically inactive S-isomer. Such racemization notably increases with increasing temperatures. Epinephrine is also rapidly destroyed in alkaline solutions by aldehydes, weak oxidizing agents, and atmospheric oxygen. Epinephrine solutions can be stored under refrigeration to reduce degradation, but longer-term stability at reduced temperature nevertheless remains a problem. Additionally, availability of refrigerated storage in doctors' offices and hospital is low, and so epinephrine solutions are not often stored in this manner. Whereas concentrated epinephrine solutions in small vials take up little room in refrigerated storage, low concentration solutions most often used for patients are often in 100 ml or 1000 ml bags, and take up valuable space if stored under refrigeration.

Epinephrine can be chemically modified to reduce degradation, however, chemical modification of catecholamines is generally undesirable for a number of reasons, including significant loss of biological activity. To overcome difficulties associated with chemical modification, antioxidants such as sodium metabisulfite or sodium bisulfite have been used to protect catecholamines or adrenergic compounds against auto-oxidation. For example, where epinephrine and sodium metabisulfite were used at a ratio of about 1:0.005 to about 1:15 by weight, formulations with desirable storage stability were obtained. However, such antioxidants have been associated in at least some cases with severe allergic reactions. In addition, sodium bisulfite can react directly with epinephrine in aqueous solution upon exposure to room light probably due to the conversion of superoxide (O2-) radicals to highly reactive hydroxyl (.OH) radicals by bisulfite (see e.g., Photo destabilization of Epinephrine by sodium metabisulfite (*PDA J Pharm Sci Technol*. 2000 March-April; 54(2):136-43). In addition, the potency of epinephrine could be further substantially degraded during shelf life storage due to radical-mediated reactions. Therefore, in view of the reactivity of epinephrine with widely used antioxidants, use of such compounds is not advisable in epinephrine containing formulations.

In yet other attempts to increase storage stability of epinephrine formulations, inclusion complexes of epinephrine with native or modified cyclodextrin derivatives have been prepared as is described in US 2018/0028671. While such compositions reduced thermal and/or oxidative degradation, the use of complexing agents rendered manufacture more difficult. Moreover, the bioavailability of the epinephrine may be reduced at least in some formulations. Furthermore, when epinephrine is diluted with water, such water often contains dissolved oxygen, as does the head space in the container. The oxygen in the water acts to degrade the epinephrine or other oxygen sensitive drug, increasing degradants and decreasing shelf life.

Therefore, even though various methods are known in the art to stabilize oxygen-sensitive drugs and specifically epinephrine in solution, numerous difficulties remain, particularly where epinephrine is present in an aqueous solution at relatively low concentrations. Consequently, there is a need for improved stable, low concentration, ready-to-administer antioxidant free epinephrine formulations, and methods of manufacture and storage of such formulations.

SUMMARY OF THE INVENTION

The inventive subject matter is directed to antioxidant free sterilizable/autoclavable and ready-to-administer compositions containing an oxygen-sensitive drug, such as epinephrine, having improved stability and a physiologically acceptable pH. As used herein, reference to the term epinephrine or any other drug should be interpreted broadly to include all pharmaceutically acceptable salts and prodrug forms thereof. Additionally, the storage systems described here can be used for solutions of other oxygen-sensitive drugs.

In one aspect of the inventive subject matter, the inventors contemplate an antioxidant-free and storage stable ready-to-administer composition containing an oxygen-sensitive drug, for example, an epinephrine composition that includes an aqueous pharmaceutically acceptable carrier containing epinephrine. Preferably, the epinephrine is present in the ready-to-administer epinephrine composition at a concentration of equal or less than about 0.07 mg/ml, and substantially all (i.e., at least about 98 mol %) of the epinephrine is an R-isomer. It is further preferred that the ready-to-administer epinephrine composition has a pH of between about 3.0 and about 4.7, and that the ready-to-administer epinephrine composition further comprises a metal ion chelator (e.g., EDTA, edetic acid, EGTA and diethylenetriaminepentaacetic acid). In further preferred aspects, the ready-to-administer epinephrine composition has, after storage of at least one month, total impurities of equal or less than about 0.7% and equal or less than about 2% S-isomer content.

For example, in some embodiments the epinephrine is present in the composition at a concentration of between about 0.005 mg/ml and about 0.050 mg/ml, or at a concentration of between about 0.006 and about 0.010 mg/ml, or at a concentration of between about 0.010 and about 0.025 mg/ml, or at a concentration of between about 0.025 and about 0.045 mg/ml. Where desired, the epinephrine is present in the composition as a pharmaceutically acceptable salt. In further embodiments, the ready-to-administer epinephrine composition has, after storage of at least one month at 25° C.+/−2° C., a pH of between about 3.5 and about 4.5, or a pH of between about 3.8 and about 4.2.

Most typically, the aqueous pharmaceutically acceptable carrier is water for injection, and may further comprise a buffer (e.g., buffer is present in a concentration of between about 1 mM and about 25 mM, buffer may be an acetate buffer, a citrate buffer, a phosphate buffer, a tartrate buffer, and a borate buffer). Contemplated compositions may also include a tonicity agent (e.g., sodium chloride, glycerol, thioglycerol, mannitol, lactose, and dextrose). Additionally, it is preferred that the ready-to-administer epinephrine composition has dissolved oxygen of equal or less than 1.5 ppm $O_2$.

In further embodiments, the ready-to-administer epinephrine composition has, after storage of at least one month at 25° C.+/−2° C., total impurities of equal or less than about 0.5% and equal or less than about 1% S-isomer content, or the ready-to-administer epinephrine composition has, after storage of at least one month at 25° C.+/−2° C., total impurities of equal or less than about 0.2% and equal or less than about 1.5% S-isomer content, or the ready-to-administer epinephrine composition has, after storage of at least one month at 25° C.+/−2° C., total impurities of equal or less than about 0.5% and equal or less than about 1% S-isomer content, or the ready-to-administer epinephrine composition has, after storage of at least one month at 25° C.+/−2° C., total impurities of equal or less than about 0.3% and equal or less than about 0.7% S-isomer content. Additionally, or alternatively, the ready-to-administer epinephrine composition has, after autoclaving, total impurities of equal or less than about 0.5% and equal or less than about 2.0% S-isomer content, or has, after autoclaving, total impurities of equal or less than about 0.2% and equal or less than about 1.5% S-isomer content.

Therefore, in yet another aspect of the inventive subject matter, the inventors also contemplate a pharmaceutical product, a polymeric container that includes the antioxidant-free and storage stable ready-to-administer composition containing an oxygen-sensitive drug, such as the epinephrine composition presented herein, wherein the container is a blow-fill-seal (BFS) container or flexible IV bag. For example, suitable polymeric containers may have a volume of between 100 mL and 1,000 mL, and may be further enclosed in a metallized over-container. Where desired, an oxygen scavenger or absorber may be disposed between the polymeric container and the metallized over-container. In still further contemplated embodiments, metallized over-container will have an oxygen transmission rate of between 0.0005 to 2.00 cc/100 $in^2$/24 hrs.

In still further aspects of the inventive subject matter, the inventors also contemplate method of producing a storage stable ready-to-administer epinephrine composition that comprises a step of combining an aqueous pharmaceutically acceptable carrier with epinephrine in an amount such that the epinephrine is present in the ready-to-administer epinephrine composition at a concentration of equal or less than about 0.07 mg/ml. Most typically, the aqueous pharmaceutically acceptable carrier has dissolved oxygen in an amount of equal or less than about 2 ppm. In another step, the pH of the ready-to-administer epinephrine composition is adjusted to a pH of between about 3.0 and about 4.7, and a metal ion chelator (e.g., EDTA, edetic acid, EGTA and diethylenetriaminepentaacetic acid) is included into the ready-to-administer epinephrine composition. In a still further step, the ready-to-administer composition containing an oxygen-sensitive drug, such as epinephrine composition is packaged into a polymeric container under an inert gas and the ready-to-administer epinephrine composition is sterilized.

For example, the step of sterilizing may comprise autoclaving, typically using saturated steam at 121° C. for at least 10 minutes, and preferably when the ready-to-administer composition containing an oxygen-sensitive drug, such as epinephrine composition is in the polymeric container. As noted earlier, the polymeric container may be further packaged into a metallized over-container.

With respect to suitable epinephrine concentrations it is contemplated that such concentrations may be between about 0.005 mg/ml and about 0.050 mg/ml, or between about 0.006 and about 0.010 mg/ml, or between about 0.010 and about 0.025 mg/ml, or between about 0.025 and about 0.045 mg/ml. As will be readily appreciated, the epinephrine may be present in the ready-to-administer composition as a pharmaceutically acceptable salt.

It is further contemplated that the ready-to-administer epinephrine composition has, after storage of at least one month at 25° C.+/−2° C., a pH of between about 3.5 and about 4.5, or between about 3.8 and about 4.2. Preferably, the aqueous pharmaceutically acceptable carrier is water for injection, which may or may not further include a buffer (e.g., acetate buffer, citrate buffer, phosphate buffer, tartrate buffer, borate buffer, typically at a concentration of between about 1 mM and about 25 mM). Where desired, a tonicity agent (e.g., sodium chloride, glycerol, thioglycerol, mannitol, lactose, dextrose) may be included into the ready-to-administer composition. Additionally, or alternatively, the ready-to-administer epinephrine composition has dissolved oxygen of equal or less than 1.5 ppm $O_2$.

In some embodiments of contemplated methods, the ready-to-administer epinephrine composition has, after storage of at least one month at 25° C.+/−2° C., total impurities of equal or less than about 0.5% and equal or less than about 1% S-isomer content, or has, after storage of at least one month at 25° C.+/−2° C., total impurities of equal or less than about 0.2% and equal or less than about 1.5% S-isomer content, or has, after storage of at least one month at 25° C.+/−2° C., total impurities of equal or less than about 0.5% and equal or less than about 1% S-isomer content. In further embodiments of contemplated methods, the ready-to-administer epinephrine composition has, after storage of at least one month at 25° C.+/−2° C., total impurities of equal or less than about 0.3% and equal or less than about 0.7% S-isomer content, or has, after sterilizing, total impurities of equal or less than about 0.5% and equal or less than about 2.0% S-isomer content, wherein the sterilizing is autoclaving, or has, after sterilizing, total impurities of equal or less than about 0.2% and equal or less than about 1.5% S-isomer content, wherein the sterilizing is autoclaving.

Various objects, features, aspects and advantages of the inventive subject matter will become more apparent from the following detailed description of preferred embodiments.

DETAILED DESCRIPTION OF THE INVENTION

The inventors have discovered that various antioxidant-free and storage stable ready-to-administer compositions containing an oxygen-sensitive drug, such as epinephrine compositions can be prepared in a relatively simple and effective manner. Advantageously, the compositions presented herein have excellent storage stability even over extended periods, and have suitably low concentrations of epinephrine that allows administration of the composition directly to a patient at a very low dosage rate (e.g., 0.05-2.0 mcg/kg/min) without prior dilution. Moreover, the inventors discovered that the compositions can be sterilized (e.g., using autoclaving) without producing undesirable quantities of biologically inactive S-isomers. Thermal stability also allows the pharmaceutical compositions to be packaged in a blow-fill-seal (BFS) process. Alternatively, the compositions presented herein can be filled into flexible infusion bags (e.g., IV).

For example, in one embodiment the antioxidant-free and storage stable ready-to-administer epinephrine composition includes an aqueous pharmaceutically acceptable carrier containing epinephrine such that epinephrine is present in the ready-to-administer epinephrine composition at a concentration of equal or less than about 0.07 mg/ml. Moreover, the ready-to-administer epinephrine composition has a pH of between about 3.0 and about 4.7, and further comprises a chelator (typically a metal ion chelator). In further embodiments, the ready-to-administer epinephrine composition has, after storage of at least one month at 25° C.+/−2° C., total impurities of equal or less than about 0.7% and equal or less than about 2% S-isomer content.

In still further embodiments, the ready-to-administer epinephrine composition is packaged in flexible infusion bags or blow-fill-seal (BFS) containers and is sterilized, preferably by autoclaving. The inventors further unexpectedly discovered that epinephrine formulations at a relatively low concentrations and a pH range of about 3.5 and about 5.0 can be subjected to terminal sterilization, and particularly sterilizing to sterility (e.g., over at least 5 minutes, or at least 10 minutes, or at least 15 min at 121° C.), without substantial increase of the S-isomer of epinephrine while being storage stable, especially when formulated with a metal ion chelator (e.g., EDTA). In further embodiments, the BFS container or flexible IV bag is further packaged in a secondary container, optionally with an oxygen scavenger, and especially a metal free oxygen scavenger. Most typically, at least one of the polymer bag and the secondary container may be impervious to light in general or light of a wavelength that promotes photo-initiated degradation. For example, suitable containers may be metalized (e.g., aluminized), or combined or coated with various carbonaceous materials or other dye(s).

In some preferred aspects, the epinephrine composition is a ready-to-administer formulation wherein epinephrine is present at a concentration of between about 0.001 to about 0.07 mg/ml, or between about 0.005 to about 0.07 mg/ml, or between about 0.005 to about 0.05 mg/ml, or between about 0.005 to about 0.03 mg/ml, or between about 0.005 to about 0.02 mg/ml. Viewed from a different perspective, while higher concentration epinephrine compositions are also contemplated, some preferred formulations will include epinephrine at a concentration of equal or less than about 0.07 mg/ml, equal or less than about 0.05 mg/ml, or even equal or less than about 0.02 mg/ml, such that no dilution is required prior to injection. Therefore, epinephrine may be present in the ready-to-administer formulation at a concentration of between about 0.005 mg/ml and about 0.050 mg/ml, or at a concentration of between about 0.006 and about 0.010 mg/ml, or at a concentration of between about 0.010 and about 0.025 mg/ml, or at a concentration of between about 0.025 and about 0.045 mg/ml.

Of course, it should be appreciated that epinephrine may be present in the composition as base or in form of a pharmaceutically acceptable salt, including a hydrochloride salt, a bitartrate salt, and a borate salt as such salt forms substantially increase the solubility of epinephrine in an aqueous medium. Moreover, it is generally preferred that substantially all of the epinephrine is in the R-isomer form (e.g., at least about 85 mol %, or at least about 90 mol %, or at least about 95 mol %, or at least about 97 mol %, or at least about 99 mol %). In still further preferred aspects, the aqueous pharmaceutically acceptable carrier is water, which may further include one or more polar and/or protic solvents that will typically form a single-phase solvent system with the water.

With further respect to the aqueous pharmaceutically acceptable carrier, it is typically preferred that the carrier and/or the ready-to-administer epinephrine composition has a dissolved oxygen content of equal or less than about 5.0 ppm or equal or less than about 3.0 ppm or equal or less than about 2.5 ppm or equal or less than about 2.0 ppm or equal or less than about 1.5 ppm or equal or less than about 1.0 ppm $O_2$ (typically during compounding and/or after 1 month of storage at 25° C.+/−2° C.). To that end, the carrier and/or ready-to-administer epinephrine composition can be subjected to sparging with an inert gas (e.g., argon, helium, freons, nitrogen, etc.), vacuum stripping under agitation, storage under an inert gas headspace, storage in a polymeric container with metallized over-container that further includes an oxygen absorber/scavenger (e.g., metal-free oxygen scavenger (e.g., GLS100, Ageless®, Pharmakeep®, all commercially available from Mitsubishi Gas Chemical America)), and/or using an enzymatic systems that deplete a solution of dissolved oxygen (see e.g., U.S. Pat. No. 9,187,779).

In other aspects of the inventive subject matter, contemplated ready-to-administer epinephrine composition can have a mildly acidic pH of between about 3.0 and about 5.5 or between about 4.0 and about 6.0, such as a pH of between about 3.5 and about 4.5 or a pH of between about 3.8 and about 4.2. Most typically the pH of the ready-to-administer epinephrine composition will be less than about 5.0 and more typically less than about 4.5, and most typically less than about 4.3, but higher than about 3.0, more typically higher than about 3.5, and most typically higher than about 3.7. As will be readily appreciated, the pH can be adjusted using various acids (e.g., HCl) and bases (e.g., NaOH). Moreover, and where desired, the pH can be stabilized using a buffer, typically at a relatively low strength. For example, suitable buffers may be present at a concentration of between about 1 mM and about 50 mM, or between about 10 mM and about 25 mM, or between about 20 mM and about 40 mM. Among other choices, contemplated buffers include organic and inorganic buffers, as well as amphoteric buffers. For example, suitable buffers include an acetate buffer, a citrate buffer, a phosphate buffer, a tartrate buffer, and a borate buffer, which may be adjusted to a pH in the range of between about 3.7 and about 4.3, or between about 3.7 and about 4.0, or between about 3.8 and about 4.1, or between about 3.9 and about 4.2, or between about 4.0 and about 4.2. Notably, such pH ranges provided remarkable stability for low concentrations of epinephrine, especially where epinephrine was combined with a chelator and optional tonicity agents.

Additionally or alternatively, the epinephrine formulations can be packaged in blow-fill-seal (BFS) containers/flexible IV bags, which are further packaged in an aluminum foil pouch or single- or multi-layer overwrap with an oxygen scavenger (secondary packaging), or aluminum pouches containing an oxygen absorbing layer (secondary packaging), where the outer pouch or packaging has an oxygen transmission rate (OTR) between 0.0005 to 0.005, or between 0.005 to 0.05, or between 0.05 to 0.5, or between 0.5 to 2.00, or between 1.0 to 5.00 cc/100 in$^2$/24 hrs.

Moreover, in further contemplated aspects, the ready-to-administer epinephrine composition will also include one or more chelating agents, and particularly metal ion chelators to slow down the baseline and metal ion-stimulated autoxidation of epinephrine. For example, suitable chelators include various bicarboxylic acids, tricarboxylic acids, and aminopolycarboxylic acids such as ethylenediaminetetraacetic acid (EDTA), ethylene glycol-bis(3-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated autoxidation of epinephrine. Notably, the inventors unexpectedly observed that the desirable effect of the chelators was observable at relatively low concentrations of the chelators. For example, reduction of the baseline and metal ion-stimulated autoxidation of epinephrine was observed at chelator concentrations of between about 1 µg/ml and about 10 µg/ml, and between about 10 µg/ml and about 100 µg/ml. Thus, preferred chelator concentrations will be between about 1 µg/ml and about 50 µg/ml, or between about 5 µg/ml and about 25 µg/ml. Interestingly, the chelators, and especially the aminopolycarboxylic acids retained stabilizing effect despite the relatively low pH favoring protonated forms of the chelators.

With respect to suitable tonicity agents, pharmaceutically acceptable salts are generally preferred to adjust/increase tonicity. For example, NaCl may be employed at a concentration of at least about 0.6 wt %, or at least about 0.7 wt %, or at least about 0.8 wt %, or at least about 0.9 wt %. Thus, suitable salt concentrations will typically be between about 0.6 wt % and about 1.2 wt %. Depending on the particular salt concentration, additional tonicity agents may be added and such suitable agents include glycerol, thioglycerol, mannitol, lactose, and dextrose. The amount of tonicity adjusting agent used can be adjusted to obtain osmolality of the formulations, typically in the range of about 260 to about 340 mOsm/kg. An osmometer can be used to check and adjust the amount of tonicity adjusting agent to be added to obtain the desired osmolality.

It should further be appreciated that contemplated compositions are substantially free of antioxidants (i.e., do not include antioxidants in an amount effective to reduce degradation of total epinephrine by at least about 1% when stored over a period of at least three months at 25° C.+/−2° C.). Therefore, and viewed from a different perspective, antioxidant-free and storage stable ready-to-administer epinephrine composition will include antioxidants in an amount of equal or less than about 0.01 wt %, or equal or less than about 0.005 wt %, or equal or less than about 0.001 wt %, or equal or less than about 0.0005 wt %, or equal or less than about 0.0001 wt %. Remarkably, despite the lack of antioxidants added to the formulation, the ready-to-administer epinephrine composition had unexpected storage stability over extended periods with regard to both oxidation/degradation and isomerization. For example, in some embodiments, the ready-to-administer epinephrine composition has, after storage of at least one month at 25° C.+/−2° C., total impurities of equal or less than about 0.7% and equal or less than about 2% S-isomer content. Moreover, and as is shown in more detail below, such storage stability extended to at least 3 months, at least 6 months, at least 9 months, at least 12 months, at least 15 months, or at least 18 months (when stored at a temperature of between about 2 and about 40° C.).

For example, certain ready-to-administer epinephrine composition had, after storage of at least one month at not less than 25° C., total impurities of equal or less than about 0.5% and equal or less than about 1% S-isomer content, or had, after storage of at least one month at 25° C.+/−2° C., total impurities of equal or less than about 0.2% and equal or less than about 1.5% S-isomer content, or had, after storage of at least one month at 25° C.+/−2° C., total impurities of equal or less than about 0.5% and equal or less than about 1% S-isomer content, or had, after storage of at least one month at 25° C.+/−2° C., total impurities of equal or less than about 0.3% and equal or less than about 0.7% S-isomer content, or had, after autoclaving, total impurities of equal or less than about 0.5% and equal or less than about 2.0% S-isomer content, or had, after autoclaving, total impurities of equal or less than about 0.2% and equal or less than about 1.5% S-isomer content.

With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave). Unexpectedly, and as shown in more detail below, the inventors have also discovered that contemplated formulations were heat stable and did not undergo significant isomerization, even under conditions of sterilization (exposure to high-pressure saturated steam) at 121° C. for at least 5, or at least 10, or at least 15 minutes. Thus, terminal sterilization to sterility is possible using contemplated compositions and methods.

Based on the unexpected heat stability, the formulations contemplated herein can also be filtered through a 0.22 micron filter, and filled in to a polyethylene, polypropylene or low-density polyethylene containers in a blow-fill-seal (BFS) process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison. The next step is the blow molding of the container with an open top through which the container is filled, all while the plastic remains hot and in a molten state. Once filled, the container is hermetically sealed and cooled. The blow-fill seal process can take several seconds, and contemplated ready-to-administer compositions advantageously are formulated to withstand the temperature and pressure requirements without substantial degradation of epinephrine (e.g., less than about 5 wt %, less than about 3 wt %, less than about 2 wt %, less than about 1 wt % degradation).

Once the epinephrine formulations are filled in large volume polymeric, semi-permeable infusion containers (e.g., BFS container or flexible IV bags), the containers can optionally be layered or covered with a secondary packaging system including an aluminum pouch or other oxygen scavenger. For example, the BFS containers can further be sealed in an oxygen and moisture barrier blister packaging. The blister packaging can comprise one or more layers, and the one or more layers can include aluminum foil or other oxygen absorber having an oxygen transmission rate (OTR) as discussed above. Additionally or alternatively, one or more oxygen absorbers (metal or metal free, organic material) can be incorporated into any portion of the BFS container, the secondary packaging system, or between the two (e.g., between the BFS container and the multi-layer packaging) such that the oxygen absorber removes at least a portion of oxygen from the air surrounding said oxygen-sensitive drug (e.g., dissolved oxygen in composition and/or oxygen in any headspace). A beneficial feature of the oxygen absorber is the absorbance and removal of oxygen present in the primary packaging and in the liquid drug itself. Notably, it was found that the oxygen absorber also removed residual headspace oxygen in the primary packaging and also dissolved oxygen in the liquid over time, thereby further improving stability of epinephrine.

For example, the polymeric container may be configured as a flexible bag with a volume of at least 100 ml, or at least 200 ml, or at least 300 ml, or at least 400 ml, or at least 500 ml, or at least 1,000 ml, wherein the polymeric bag may be manufactured from polyvinyl chloride, polyethylene, polypropylene, polyethylene terephthalate, various co-polymers such as ethylene-propylene copolymers, ethylene vinyl acetate, copolyester ether polymers, etc. Such polymeric containers may preferably, but not necessarily have a reduced oxygen permeability (e.g., where no overwrap is used). These containers or bags may then preferably packaged into an overwrap (or other secondary package) that has one or more additional properties that help maintain stability. For example, additional properties include light-absorbing or non-transparent films to block or at least significantly reduce ingress of light of a wavelength and/or energy sufficient to initiate photolytic degradation. Other additional properties include reduced oxygen permeability that can be achieved in a variety of manners, including multi-layered polymer and/or metal films that may also include oxygen scavenging materials. For example, a suitable overwrap may comprise a polypropylene base layer that is coupled to a thin aluminum layer (e.g., thickness between 10 and 50 micrometer), which may be covered by an oriented polyester layer (e.g., commercially available as MEDIFLEX AUAT™ from Amcor Flexibles, Gent, Belgium).

The commercially available and concentrated formulation, Epinephrine Injection USP (1 mg/mL) will after dilution in dextrose or dextrose and sodium chloride injections quickly develop colored impurities. In contrast, and as is shown in more detail below, the antioxidant-free and storage stable ready-to-administer epinephrine compositions presented herein are stable over extended periods at room temperature as well as under refrigeration (e.g., temperature between about 2 and about 8° C.). Impurities resulting from chemical reactions in solution remain within acceptable limits (e.g., less than about 10 wt %, less than about 5 wt %, less than about 4 wt %, less than about 3 wt %, less than about 2 wt %, less than about 1 wt %) over long term storage (e.g., at least 1 month, at least 2 months, at least 3 months, at least 6 months, at least 9 months, at least 12 months, at least 18 months). Therefore, epinephrine formulations of the inventive subject matter can be provided in a ready-to-administer form to avoid the inconvenience associated with diluting a concentrated small volume epinephrine parenteral formulation into infusion diluents prior to infusion. The ready-to-administer formulations also eliminate microbial contamination risks and calculation errors associated with dilution. In certain aspects of the inventive subject matter, contemplated formulations will be available in a range of concentrations commonly required by medical practitioners for emergency restoration of blood pressure in cases of acute hypotension. Thus, ready-to-administer formulations are formulations that can be administered to a patient in need thereof without prior dilution (typically at the point of care such as a hospital or physician office) from a previously stored solution having a higher epinephrine concentration. Viewed from a different perspective, the ready-to-administer formulations presented herein can be received and stored at a care facility, and then directly used for administration without prior dilution.

The following examples are provided for illustrative purposes only and should not be interpreted as limiting the present invention.

Examples

The following examples illustrate some of the experiments leading to the formulations according to the inventive subject matter, however, should not be construed to limit the scope of the claims in any way.

The stability of epinephrine formulation at different pH conditions, ranging from 3.5 to 5.0 was studied at different temperature conditions of, 25° C., 40° C., and 60° C. All formulations were prepared under similar conditions, and formulation details are given in Table 1. The formulations were analyzed for appearance, pH, and assay. The results of the stability studies are presented in Tables 2-5.

For preparation of the solutions, about 90% of the final quantity of water was collected in a glass media bottle. Nitrogen ($N_2$) gas was purged for about thirty minutes to reduce dissolved oxygen. Sodium chloride was added and the solution was stirred until a homogenous solution was obtained. The pH of the bulk solutions was adjusted to pH 3.5, 4.0, 4.5, and 5.0 respectively for each formulation composition using sufficient quantity of sodium hydroxide or hydrochloric acid. Epinephrine was added and the solution was stirred for approximately 10 minutes until a clear solution was formed. Solutions were made up to volume with water.

TABLE 1

| Ingredients | Example 1 RD-043-018A Qty/mL (mg) | Example 2 RD-043-018B Qty/mL (mg) | Example 3 RD-043-018C Qty/mL (mg) | Example 4 RD-043-018D Qty/mL (mg) |
|---|---|---|---|---|
| Epinephrine | 0.016 | 0.016 | 0.016 | 0.016 |
| Sodium Chloride | 9.0 | 9.0 | 9.0 | 9.0 |
| Disodium Edetate | 0.01 | 0.01 | 0.01 | 0.01 |
| Sodium Hydroxide | q.s. | q.s. | q.s. | q.s. |
| Hydrochloric Acid | q.s. | q.s. | q.s. | q.s. |
| Vehicle | q.s. 1 mL | q.s. 1 mL | q.s. 1 mL | q.s. 1 mL |
| pH | 3.5 | 4.0 | 4.5 | 5.0 |

TABLE 2

Results for RD-043-018A, pH 3.5 (Example 1)

| | | 25° C. ± 2° C./60% RH ± 5% RH | | | | | 40° C. ± 2° C./75% RH ± 5% RH | | | | |
|---|---|---|---|---|---|---|---|---|---|---|---|
| TEST | Initial | 3 Day | 1 Wk. | 2 Wks. | 3 Wks. | 4 Wks. | 3 Day | 1 Wk. | 2 Wks. | 3 Wks. | 4 Wks |
| Appearance | Clear colorless solution | Clear colorless solution | Clear colorless solution | Clear colorless solution | Clear colorless solution | Clear colorless solution | Clear colorless solution | Clear colorless solution | Clear colorless solution | Clear colorless solution | Clear colorless solution |
| pH | 3.58 | 3.64 | 3.62 | 3.64 | 3.76 | 3.69 | 3.65 | 3.63 | 3.63 | 3.71 | 3.73 |
| Assay | 100.10 | 99.67 | 98.26 | 99.60 | 97.88 | 99.63 | 99.43 | 98.41 | 98.95 | 97.35 | 97.98 |

For Example 1, it was observed that the formulation was stable physically, as there was no change in the appearance, pH and assay of the formulation at 25° C. and 40° C. at the end of 4 weeks when compared to initial.

TABLE 3

Results for RD-043-018B, pH 4.0 (Example 2)

| | | 25° C. ± 2° C./60% RH ± 5% RH | | | | | 40° C. ± 2° C./75% RH ± 5% RH | | | | |
|---|---|---|---|---|---|---|---|---|---|---|---|
| TEST | Initial | 3 Day | 1 Wk. | 2 Wks | 3 Wks | 4 Wks. | 3 Day | 1 Wk. | 2 Wks. | 3 Wks. | 4 wks |
| Appearance | Clear colorless solution | Clear colorless solution | Clear colorless solution | Clear colorless solution | Clear colorless solution | Clear colorless solution | Clear colorless solution | Clear colorless solution | Clear colorless solution | Clear colorless solution | Clear colorless solution |
| pH | 4.35 | 4.30 | 3.68 | 4.23 | 4.34 | 4.41 | 4.38 | 4.41 | 4.36 | 4.53 | 4.34 |
| Assay | 99.33 | 98.09 | 97.69 | 99.05 | 96.64 | 97.65 | 97.99 | 98.33 | 95.90 | 92.34 | 79.38 |

For Example 2, it was observed that the formulation was stable physically, at 25° C. and 40° C. for 4 weeks as there was no significant change in the pH, appearance and assay of the formulation.

TABLE 4

Results for RD-043-018C, pH 4.5 (Example 3)

| | | 25° C. ± 2° C./60% RH ± 5% RH | | | | | 40° C. ± 2° C./75% RH ± 5% RH | | | | |
|---|---|---|---|---|---|---|---|---|---|---|---|
| TEST | Initial | 3 Day | 1 Wk. | 2 Wks. | 3 Wks. | 4 Wks. | 3 Day | 1 Wk. | 2 Wks. | 3 Wks. | 4 wks. |
| Appearance | Clear colorless solution | Clear colorless solution | Clear colorless solution | Clear colorless solution | Slight pink | Slight brown | Clear colorless solution | Clear colorless solution | Slight brown | Slight brown | Slight brown |
| pH | 4.35 | 5.17 | 4.97 | 4.89 | 4.83 | 4.82 | 5.03 | 5.07 | 5.00 | 4.50 | 4.70 |
| Assay | 97.22 | 97.86 | 99.12 | 89.64 | 87.53 | 83.19 | 97.97 | 94.87 | 65.27 | 66.76 | 58.52 |

For example 3, it was observed that the formulation was not stable at pH 4.5. A change in the visual appearance was observed at 25° C. and 40° C. conditions. Also the drug formulation showed decreasing assay numbers with increase in the duration of storage as compared to examples 1 and 2.

TABLE 5

Results RD-043-018D, pH 5.0 (Example 4)

| | | 25° C. ± 2° C./60% RH ± 5% RH | | | | | 40° C. ± 2° C./75% RH ± 5% RH | | | | |
|---|---|---|---|---|---|---|---|---|---|---|---|
| TEST | Initial | 3 Day | 1 Wk. | 2 Wks. | 3 Wks. | 4 Wks. | 3 Day | 1 Wk. | 2 Wks. | 3 Wks. | 4 wks. |
| Appearance | Clear colorless solution | Clear colorless solution | Clear colorless solution | Clear colorless solution | Slight pink | Slight pink | Light brown | Light pink | Slight brown | Slight brown | Slight brown |
| pH | 5.15 | 5.40 | 5.95 | 5.01 | 5.17 | 5.22 | 5.66 | 5.08 | 5.22 | 4.44 | 4.40 |
| Assay | 96.50 | 99.84 | 104.33 | 68.70 | 73.94 | 67.45 | 102.01 | 93.20 | 59.39 | 36.63 | 36.02 |

For example 4, significant change in the visual appearance and assay was observed at 25° C. and 40° C. when compared to Example 1, Example 2 and Example 3. The inventor found that the formulation was more stable at pH 3.5-4.0, as compared to pH 4.5 and 5.0. As the pH of the formulation was increased, the stability of the formulation decreased.

The presence of atmospheric oxygen promotes the oxidation rate of epinephrine. Since oxidation frequently involves free radicals, chain reactions occur. Light provides the necessary energy to initiate the oxidation process of epinephrine. Therefore, further experiment was performed in Water for Injection as vehicle, EDTA as chelating agent, and controlled overhead space using flexible IV bags which were further packaged in an aluminum foil pouch with an oxygen scavenger (secondary packaging) or other aluminum pouches containing an oxygen absorbing layer (secondary packaging) as final packaging. The ready-to-administer solutions of example 5 (Table 6) was prepared according to the above procedure of Example 1-4 with head space oxygen levels controlled (i.e., replaced by inert gas) during compounding.

All final formulation filling was performed under inert gas atmosphere. To prevent further oxidation degradation, the inventors controlled head space oxygen in the range of 0.1% to 20%. This was achieved by purging head space with inert gas as explained above. The formulation solution was filled in the flexible IV bags and then placed in an aluminum bag with an oxygen scavenger (secondary packaging) and sealed. The sealed bags were then kept for stability study at 25° C. and 40° C. The results of the stability study of Example 5 are provided in Table 7.

TABLE 6

Example 5

| Ingredients | Qty/mL (mg) |
| --- | --- |
| Epinephrine | 0.016 |
| Sodium Chloride | 9.0 |
| EDTA | 0.01 |
| Sodium Hydroxide | q.s. |
| Hydrochloric Acid | q.s. |
| Vehicle | q.s. 1 mL |
| pH | 4.0 ± 0.2 |

TABLE 7

Results for RD-043-001 (Example 5)

| | | 25° C. ± 2° C./60% RH ± 5% RH | | 40° C. ± 2° C./75% RH ± 5% RH | |
| --- | --- | --- | --- | --- | --- |
| TEST | Initial | 1 Month | 3 Months | 1 Month | 3 Months |
| Appearance | Clear colorless solution | Clear colorless solution | Clear colorless solution | Clear colorless solution | Clear colorless solution |
| Color  L | NT | 99 | 99.8 | 99.9 | 99.8 |
| Change a | NT | 0.0 | 0.0 | 0.0 | 0.0 |
|        b | NT | 0.0 | 0.0 | 0.0 | 0.0 |
| pH | 3.64 | 3.70 | 3.68 | 3.73 | 4.26 |
| Assay (%) | 103.7 | 102.74 | 101.55 | 103.11 | 101.75 |
| Total Impurities (%) | 0.140 | 0.325 | 0.511 | 0.690 | 0.703 |

NT—Not tested

It was found in Example 5 formulation, for 3 months at 25° C. and 40° C. temperature (accelerated conditions) that epinephrine ready-to-administer formulations remained clear and colorless, without any signs of precipitation or color change upon storage. The pH of the formulation did not change significantly at different temperature conditions. There was no significant change in the assay of the formulation, which clearly indicates the formulation is very stable.

Further the inventors studied the effect of autoclaving on the formation of S (+) isomer which is the inactive form in the formulation. Example 6 was subjected to autoclaving at 121° C. for 15 minutes. The autoclaved vs non-autoclaved samples were analyzed for assay and related substances and for the formation of S (+) isomer. Example 6 formulation was prepared similar to Example 1 and 2. Table 8 shows the composition of Example 6. The results are shown in Table 9.

TABLE 8

Example 6

| Ingredients | Lot # 10358 Qty/mL (mg) | Lot # 10359 Qty/mL (mg) |
| --- | --- | --- |
| Epinephrine | 0.008 | 0.032 |
| Sodium Chloride | 9.0 | 9.0 |
| Disodium Edetate | 0.01 | 0.01 |
| Sodium Hydroxide | q.s. | q.s. |
| Hydrochloric Acid | q.s. | q.s. |
| Water for Injection | q.s. 1 mL | q.s. 1 mL |

TABLE 9

| | Lot # 10358 | | Lot # 10359 | |
| --- | --- | --- | --- | --- |
| Test Parameters | Non-autoclaved | Autoclaved | Non-autoclaved | Autoclaved |
| Assay | 100.267 | 100.779 | 100.312 | 103.395 |
| % S form | 0.00 | 2.403 | 0.00 | 1.996 |
| Total Impurities | 0.23 | 0.62 | 0.23 | 0.37 |

The inventors therefore concluded that (i) water for injection is a good vehicle which improves ready-to-administer Epinephrine solution stability; (ii) at higher pH, the stability of ready-to-administer formulation decreases (iii) controlled head space oxygen levels of <1% helped in improving the stability of the ready-to-administer solution of Epinephrine. Moreover, stability was remarkably high even at very low chelator concentration.

In still further experiments, the inventors prepared various epinephrine formulations as shown in Table 10, which included tartrate as a further component, and exemplary results for the stability of these formulations are provided in Table 11 (16 mcg/mL, non-terminally sterilized) and Table 12 (16 mcg/mL, terminally sterilized).

TABLE 10

| Ingredient | Purpose | NVK-019 Formulations | | | | |
|---|---|---|---|---|---|---|
| Epinephrine | Active pharmaceutical Ingredient | 8 mcg/mL | 16 mcg/mL | 20 mcg/mL | 32 mcg/mL | 40 mcg/mL |
| Sodium chloride | Isotonicity adjusting agent | 9 mg/mL | 9 mg/mL | 9 mg/mL | 9 mg/mL | 9 mg/mL |
| Disodium Edetate dihydrate (EDTA) | Metal chelator/ stabilizer | 0.01 mg/mL | 0.01 mg/mL | 0.01 mg/mL | 0.01 mg/mL | 0.01 mg/mL |
| Tartaric Acid | Buffering agent | 6.6 mcg/mL | 13.1 mcg/mL | 16.4 mcg/mL | 26.2 mcg/mL | 32.8 mcg/mL |
| Hydrochloric acid/sodium hydroxide | pH adjusting agent | Q.S. to adjust pH to 4.0 | | | | |
| Water | Vehicle | Q.S. to 1 mL | | | | |

TABLE 11

| | | TIME POINT | | | | | | | | |
|---|---|---|---|---|---|---|---|---|---|---|
| | | | 25° C. ± 2° C./ 60% RH ± 5% RH | | | | 40° C. ± 2° C./75% RH ± 5% RH | | | |
| TEST | | Initial | 1 M | 2 M | 3 M | 4 M | 1 M | 2 M | 3 M | 4 M |
| Appearance | | Clear Colorless solution | Clear Colorless solution | Clear Colorless solution | Clear Colorless solution | Clear Colorless solution | Clear Colorless solution | Clear Colorless solution | Clear Colorless solution | Clear Colorless solution |
| Color of solution | L | 100.9 | 99.9 | 100 | 99.8 | 99.9 | 100 | 100 | 99.9 | 96.3 |
| | a | 0 | 0 | -0.1 | 0 | 0 | 0 | 0 | 0 | 0 |
| | b | 0.4 | 0.1 | 0 | 0.1 | 0.1 | 0 | 0 | 0.1 | -1.6 |
| pH | | 4.24 | 4.24 | 4.24 | 4.14 | 4.14 | 4.25 | 4.26 | 4.21 | 4.23 |
| Dissolved Oxygen (ppm) | | 0.61 | 0.66 | 0.83 | 0.72 | 0.79 | 0.84 | 1.41 | 0.84 | 0.97 |
| Assay of Epinephrine (%) | | 98.0 | 98.1 | 98.1 | 98.8 | 97.0 | 99.1 | 98.7 | 98.9 | 96.7 |
| Related Substances (%) | RRT -1.24 | ND | 0.10 | 0.07 | 0.10 | 0.09 | 0.10 | 0.09 | 0.12 | 0.13 |
| | RRT-1.28 | 0.07 | 0.04 | ND | 0.04 | 0.03 | 0.05 | 0.05 | 0.08 | 0.09 |
| | RRT -1.30 | 0.13 | 0.22 | 0.25 | 0.06 | ND | 0.12 | 0.03 | 0.09 | ND |
| | RRT-3.46 | 0.1 | ND | ND | ND | ND | ND | ND | ND | ND |
| | RRT - 4.04 | ND | ND | ND | ND | ND | 0.07 | ND | ND | ND |
| Total Impurities (%) | | 0.3 | 0.4 | 0.3 | 0.2 | 0.1 | 0.3 | 0.2 | 0.3 | 0.2 |
| S-Isomer Content (%) | | 0.2 | 0.4 | 0.4 | 0.6 | 0.9 | 0.9 | 1.4 | 2.3 | 3.1 |

Note:
Impurities ≤0.0554 are not reported

TABLE 12

| | | TIME POINT | | | | | | |
|---|---|---|---|---|---|---|---|---|
| | | Initial | | 25° C. ± 2° C./60% RH ± 5% RH | 40° C. ± 2° C./75% RH ± 5% RH | 60° C. | | |
| | | Prior to Autoclaving | After Autoclaving | 1 Month | 1 Month | 1 week | 3 weeks | 1 month |
| TEST | | | | | | | | |
| Appearance | | Clear colorless solution | Clear colorless solution | Clear colorless solution | Clear colorless solution | Clear colorless solution | Clear colorless solution | Clear colorless solution |
| pH | | 3.78 | 3.76 | 3.91 | 3.89 | 3.77 | 3.75 | 3.89 |
| Dissolved Oxygen (ppm) | | 1.09 | 1.74 | 1.25 | 1.37 | 0.77 | 0.48 | 0.7 |
| Color of solutio | L | 99.9 | 99.9 | 103.4 | 103 | 99.1 | 100 | 101.8 |
| | a | 0 | 0 | 0 | 0 | 0.1 | 0 | 0.3 |
| | b | -0.1 | 0 | -1.4 | -1.4 | 0 | 0.1 | -1.8 |
| Assay of Epinephrine (%) | | 100.9 | 100.9 | 102.1 | 101.1 | 100.9 | 101.9 | 100.8 |
| Related Substances (%) | RRT- 1.20 | 0.04 | 0.06 | 0.09 | 0.09 | 0.15 | 0.16 | 0.17 |
| | RRT- 1.24 | 0.08 | 0.02 | ND | ND | ND | ND | ND |
| | RRT - 1.26 | ND | 0.07 | ND | ND | 0.15 | ND | ND |
| | RRT - 1.29 | ND | ND | 0.04 | 0.05 | ND | 0.14 | 0.16 |
| | RRT - 2.95 | ND | ND | ND | ND | ND | 0.06 | 0.08 |
| Total Impurities (%) | | 0.1 | 0.2 | 0.1 | 0.1 | 0.3 | 0.4 | 0.4 |
| S-Isomer content (%) | | 0.3 | 1.5 | 0.7 | 1.4 | 3.8 | 8.1 | 10.2 |

Note:
Impurities ≤0.05% are not reported

Similarly, in additional experiments, the inventors prepared unbuffered epinephrine formulations as shown in Table 13 (without tartrate), and exemplary results for the stability of these formulations are provided in Table 14 (16 mcg/mL, non-terminally sterilized) and Table 15 (16 mcg/mL, terminally sterilized).

TABLE 13

| Ingredient | Purpose | NVK-019 Formulations | | | | |
|---|---|---|---|---|---|---|
| Epinephrine | Active pharmaceutical Ingredient | 8 mcg/mL | 16 mcg/mL | 20 mcg/mL | 32 mcg/mL | 40 mcg/mL |
| Sodium chloride | Isotonicity adjusting agent | 9 mg/mL | 9 mg/mL | 9 mg/mL | 9 mg/mL | 9 mg/mL |
| Disodium Edetate dihydrate (EDTA) | Metal chelator/ stabilizer | 0.01 mg/mL | 0.01 mg/mL | 0.01 mg/mL | 0.01 mg/mL | 0.01 mg/mL |
| Hydrochloric acid/sodium hydroxide | pH adjusting agent | Q.S. to adjust pH to 4.0 | | | | |
| Water | Vehicle | Q.S. to 1 mL | | | | |

TABLE 14

| TEST | | Initial | 25° C. ± 2° C./60% RH ± 5% RH | | | | 40° C. ± 2° C./75% RH ± 5% RH | | | |
|---|---|---|---|---|---|---|---|---|---|---|
| | | | 1 M | 2 M | 3 M | 4 M | 1 M | 2 M | 3 M | 4 M |
| Appearance | | Clear Colorless solution | Clear Colorless solution | Clear Colorless solution | Clear Colorless solution | Clear Colorless solution | Clear Colorless solution | Clear Colorless solution | Clear Colorless solution | Clear Colorless solution |
| Color of solution | L | 100 | 99.9 | 100 | 99.8 | 99.9 | 100 | 100.1 | 99.9 | 99.9 |
| | a | 0 | 0 | 0 | 0 | 0 | 0 | 0 | 0 | -0.1 |
| | b | -0.3 | 0 | 0 | 0 | 0.1 | 0 | 0 | 0 | 0 |
| pH | | 4.03 | 4.03 | 3.90 | 3.94 | 3.94 | 4.04 | 4.06 | 3.98 | 4.01 |
| Dissolved Oxygen (ppm) | | 1.52 | 0.82 | 1.17 | 0.91 | 1.00 | 0.70 | 1.22 | 0.87 | 0.74 |
| Assay of Epinephrine (%) | | 98.7 | 99.8 | 98.9 | 99.4 | 99.1 | 99.6 | 99.1 | 99.9 | 98.1 |
| Related Substances (%) | RRT-1.242 | ND | 0.07 | 0.12 | 0.09 | 0.12 | 0.07 | 0.20 | 0.21 | 0.25 |
| | RRT -1.288 | ND | ND | 0.04 | ND | 0.04 | ND | 0.11 | 0.12 | 0.13 |
| | RRT- 1.40 | ND | ND | ND | ND | 0.08 | ND | ND | ND | ND |
| | RRT - 1.305 | 0.15 | 0.31 | 0.26 | 0.11 | 0.03 | 0.12 | 0.03 | 0.25 | ND |
| | RRT- 3.463 | 0.15 | ND | ND | ND | ND | ND | ND | ND | ND |
| | RRT - 4.044 | ND | 0.08 | ND | ND | ND | 0.09 | ND | ND | ND |
| Total Impurities (%) | | 0.3 | 0.5 | 0.4 | 0.2 | 0.3 | 0.3 | 0.3 | 0.6 | 0.4 |
| S-Isomer content (%) | | 0.2 | 0.3 | 0.5 | 0.6 | 0.8 | 1.0 | 1.6 | 2.5 | 3.3 |

TABLE 15

| TEST | | Initial | | 25° C. ± 2° C./60% RH ± 5% RH | 40° C. ± 2° C./75% RH ± 5% RH | 60° C. | | |
|---|---|---|---|---|---|---|---|---|
| | | Prior to Autoclaving | After Autoclaving | 1 month | 1 month | 1 week | 3 weeks | 1 month |
| Appearance | | Clear Colorless solution | Clear Colorless solution | Clear Colorless solution | Clear Colorless solution | Clear Colorless solution | Clear Colorless solution | Clear Colorless solution |
| pH | | 4.03 | 3.93 | 3.99 | 4.02 | 3.95 | 3.95 | 3.98 |
| Dissolved Oxygen (ppm) | | 1.38 | 1.41 | 0.95 | 0.69 | 0.92 | 0.68 | 0.88 |
| Color of solution | L | 100 | 100.3 | 103.5 | 103.5 | 100 | 99.1 | 103.4 |
| | a | 0 | 0.1 | 0 | 0 | 0 | 0.1 | 0 |
| | b | 0 | -0.1 | -1.4 | -1.4 | 0 | 0.1 | -1.3 |
| Assay of Epinephrine (%) | | 102.8 | 101.8 | 99.9 | 99.9 | 100.4 | 100.6 | 98.6 |
| Related Substances (%) | RRT - 1.20 | 0.02 | 0.04 | 0.07 | 0.08 | 0.09 | 0.14 | 0.12 |
| | RRT- 1.24 | 0.10 | 0.08 | 0.10 | ND | ND | ND | ND |
| | RRT - 1.29 | ND | ND | 0.05 | 0.06 | ND | 0.14 | 0.12 |
| | RRT - 1.46 | 0.12 | 0.11 | 0.11 | 0.12 | 0.11 | 0.13 | 0.14 |
| Total Impurities (%) | | 0.2 | 0.2 | 0.3 | 0.3 | 0.20 | 0.4 | 0.4 |
| S-Isomer content (%) | | 0.3 | 0.6 | 0.7 | 1.4 | 2.7 | 7.8 | 9.2 |

Similarly, Tables 16, 17, 18 depict exemplary results for epinephrine compositions as shown in Table 13, with epinephrine concentrations of 20 mcg/mL, 32 mcg/mL, and 40 mcg/mL, respectively, all after terminal sterilization.

TABLE 16

| | | TIME POINT | | | | |
|---|---|---|---|---|---|---|
| | | | 25° C. ± 2° C./60% RH ± 5% RH | 40° C. ± 2° C./75% RH ± 5% RH | 60° C. | |
| TEST | | Initial | 2 Wks. | 2 Wks. | 1 Wk. | 2 Wks. |
| | Appearance | Clear Colorless solution | Clear Colorless solution | Clear Colorless solution | Clear Colorless solution | Clear Colorless solution |
| | pH | 4.18 | 4.06 | 4.08 | 4.03 | 4.06 |
| | DO (ppm) | 2.16 | 0.65 | 0.84 | 0.66 | 0.73 |
| Color of solution | L* | 100 | 100.1 | 100.1 | 100.1 | 99.9 |
| | a* | 0 | 0 | 0 | 0.1 | 0 |
| | b* | 0.1 | −0.1 | −0.1 | 0 | 0 |
| | Assay | 100.476 | 99.223 | 100.116 | 97.854 | 99.129 |
| Related Substances (%) | RRT- 1.219 | NR | ND | ND | ND | ND |
| | RRT- 1.239 | NR | 0.058 | 0.087 | 0.092 | 0.110 |
| | RRT- 1.306 | 0.063 | 0.055 | 0.088 | 0.116 | 0.137 |
| | RET- 1.367 | NR | NR | NR | NR | NR |
| | RRT- 1.42 | NR | ND | ND | ND | ND |
| | RRT- 1.863 | ND | ND | ND | 0.050 | ND |
| | RRT-2.53 | ND | 0.055 | 0.058 | NR | 0.051 |
| | RRT-2.93 | ND | ND | ND | ND | 0.060 |
| | RRT- 3.450 | 0.097 | 0.074 | 0.073 | 0.109 | ND |
| Total Impurities (%) | | 0.160 | 0.252 | 0.306 | 0.367 | 0.358 |
| S-Isomer Content (%) | | 1.058 | 1.205 | 1.443 | 4.203 | 6.012 |

TABLE 17

| | | TIME POINT | | | | |
|---|---|---|---|---|---|---|
| | | | 25° C. ± 2° C./60% RH ± 5% RH | 40° C. ± 2° C./75% RH ± 5% RH | 60° C. | |
| TEST | | Initial | 2 Wks. | 2 Wks. | 1 Wk. | 2 Wks. |
| | Appearance | CCS | CCS | CCS | CCS | CCS |
| | pH | 4.13 | 4.06 | 4.05 | 4.02 | 4.07 |
| | DO (ppm) | 2.34 | 0.90 | 0.71 | 0.68 | 0.95 |
| Color | L* | 100.5 | 100.3 | 100.3 | 100 | 100.1 |
| | a* | 0 | 0 | 0 | 0 | 0 |
| | b* | −0.1 | −0.1 | 0 | 0 | 0 |
| | Assay | 100.67 | 100.670 | 99.575 | 99.138 | 100.232 |
| Related Substances | RRT- 1.113 | ND | ND | ND | 0.058 | ND |
| | RRT- 1.239 | NR | NR | 0.055 | NR | 0.085 |
| | RRT - 1.306 | 0.077 | 0.069 | 0.080 | 0.104 | 0.121 |
| | RRT - 1.38 | ND | ND | ND | ND | 0.093 |
| | RRT -1.42/1.40 | ND | ND | ND | 0.088 | ND |
| | RRT - 1.95 | 0.172 | ND | ND | ND | 0.184 |
| | RRT-2.53 | NR | 0.052 | 0.058 | 0.053 | 0.061 |
| | RRT- 2.93 | 0.076 | ND | ND | NR | 0.063 |
| | RRT - 3.450 | 0.135 | 0.074 | ND | 0.080 | ND |
| Total Impurities (%) | | 0.460 | 0.195 | 0.193 | 0.383 | 0.607 |
| S-Isomer content (%) | | 2.201 | 2.201 | 2.419 | 5.077 | 7.077 |

TABLE 18

| | | TIME POINT | | | | |
|---|---|---|---|---|---|---|
| | | | 25° C. ± 2° C./60% RH ± 5% RH | 40° C. ± 2° C./75% RH ± 5% RH | 60° C. | |
| TEST | | Initial | 2 Wks. | 2 Wks. | 1 Wk. | 2 Wks. |
| | Appearance | CCS | CCS | CCS | CCS | CCS |
| | pH | 4.14 | 4.07 | 4.07 | 4.05 | 4.08 |
| | DO (ppm) | 1.83 | 0.97 | 0.60 | 0.60 | 0.81 |

TABLE 18-continued

| | | TIME POINT | | | | |
|---|---|---|---|---|---|---|
| | | 25 C. 25° C. ± 2° C./60% RH ± 5% RH | 40° C. ± 2° C./75% RH ± 5% RH | | 60° C. | |
| | TEST | Initial | 2 Wks. | 2 Wks. | 1 Wk. | 2 Wks. |
| Color | L* | 100.2 | 100.1 | 100.1 | 100 | 100 |
| | a* | 0 | 0 | 0 | 0 | 0.1 |
| | b* | 0 | 0 | 0 | 0 | 0.1 |
| | Assay | 98.028 | 99.880 | 99.832 | 98.620 | 99.326 |
| Related substances | RRT - 1.219 | 0.050 | ND | ND | ND | ND |
| | RRT - 1.239 | ND | NR | 0.071 | 0.080 | 0.084 |
| | RRT - 1.306 | ND | 0.097 | 0.116 | 0.133 | 0.133 |
| | RRT - 1.32 | 0.090 | ND | ND | ND | ND |
| | RRT - 1.42/1.38 | ND | ND | ND | ND | 0.094 |
| | RRT - 1.863 | ND | ND | ND | 0.054 | ND |
| | RRT - 1.91 | ND | ND | | 0.072 | ND |
| | RRT - 2.58 | 0.053 | 0.07 | 0.065 | 0.061 | 0.062 |
| | RT - 2.93 | ND | ND | ND | ND | 0.059 |
| | RRT - 3.450 | 0.128 | 0.047 | ND | ND | ND |
| Total Impurities (%) | | 0.321 | 0.214 | 0.252 | 0.400 | 0.432 |
| S-Isomer Content (%) | | 2.713 | 3.124 | 3.362 | 5.687 | 7.357 |

Notably, the above series of experiments demonstrated an unexpected stability of the low-concentration epinephrine formulations with respect to lack of isomerization (even when terminally sterilized) and with respect to degradation/oxidation products for both the epinephrine base and the epinephrine tartrate salt forms. While not wishing to be bound by any particular theory or hypothesis, the inventors contemplate that the stability of the epinephrine in the low-concentration formulations (i.e., equal or less than about 50 mcg/mL, or equal or less than about 40 mcg/mL, or equal or less than about 32 mcg/mL, or equal or less than about 20 mcg/mL, or equal or less than about 16 mcg/mL, or equal or less than 8 mcg/mL) was at least in part attributable to the low-concentration of a chelator (e.g., equal or less than about 30 mcg/mL, or equal or less than about 20 mcg/mL, or equal or less than about 10 mcg/mL), the specific pH range (e.g., between about 3.65 and about 4.25, or between about 3.75 and about 4.50) at relatively low quantities of dissolved $O_2$ (e.g., equal or less than about 1.8 ppm, or equal or less than about 1.6 ppm, or equal or less than about 1.4 ppm, or equal or less than about 1.2 ppm, or equal or less than about 1.0 ppm, or equal or less than about 0.8 ppm). Unless noted otherwise, all results for terminal sterilization were from materials packaged in a polymer bag and an overpackage, with an oxygen scavenger disposed between the polymer bag and the overpackage.

Identification, Assay and Determination of Related Compounds of Epinephrine in Epinephrine Injection by HPLC-UV: In general, separation of Epinephrine (EPI) and related compounds is performed using a gradient HPLC method with the UV detection. Pentafluorophenylpropyl terminated silica is used as a stationary phase for chromatographic analysis. The mobile phase is prepared by mixing an aqueous formate buffer and mixture of methanol-acetonitrile. EPI is identified based on the retention time of the major peak in a Sample solution chromatogram as compared to that from a Reference Standard (RS) solution chromatogram. Quantitation of EPI is accomplished by comparing corresponding peak areas from the Sample solution chromatogram and from the RS solution chromatogram. Related compounds are defined by their retention times (RT) based on the RT data for a Peak Identification Mixture. Quantitation of the related compounds is accomplished by comparing the corresponding peak area from the Sample Solution chromatogram to the EPI peak area from the RS solution chromatogram.

The HPLC system was equipped with a quaternary pump or a binary pump, a degasser, auto sampler, a thermo-stated column compartment, and a DAD detector with a 60 mm cell: Agilent 1260 HPLC with a detector having a Max-Light 60 mm Optical Path Length Cell, or equivalent. Mobile Phase A was 25 mM Ammonium formate buffer pH 3 in water, and Mobile Phase B was 90:10 v/v Methanol/Acetonitrile. Chromatographic conditions are shown in Table 16 below.

TABLE 16

| HPLC | Agilent 1260 HPLC or equivalent |
|---|---|
| Column | Supelco Discovery HS F5-5 Column, 5 μm, 4.6 × 250 mm |
| Column Temperature | 35 ± 2° C. |
| Sample Temperature | 5 ± 5° C. |
| Injection volume | 80.0 μL |
| Flow Rate | 1.0 mL/min |
| Detection | DAD detector with 60 mm Optical Path Length Cell Spectrum: 200-600 nm, resolution 1.0 nm Single channel: 280 nm, resolution 4.0 nm Sampling Rate: 5 Hz |
| Mobile Phase A | 25 mM Ammonium Formate Buffer pH 3 in Water |
| Mobile Phase B | 90:10 v/v Methanol/Acetonitrile |

| Gradient | Time (min) | Solution A (%) | Solution B (%) |
|---|---|---|---|
| | 0.0 | 99.0 | 1.0 |
| | 4.0 | 99.0 | 1.0 |
| | 10.0 | 90.0 | 10.0 |
| | 40.0 | 50.0 | 50.0 |
| | 43.0 | 50.0 | 50.0 |
| | 43.1 | 99.0 | 1.0 |
| | 50.0 | 99.0 | 1.0 |

Epinephrine Assay: The EPI concentration in the Sample Solution, $C_{Smp}$ (mcg/mL), is calculated using Eqs. 1 and 2.

$$C_{WS} = \frac{W_{WS}}{V_{Stock}} \times \frac{V_1}{V_{WS}} \times \frac{M_1}{M_2} \times P \times 1000 \text{ mcg/mg}, \quad (1)$$

$$C_{Smp} = \frac{R_{Smp}}{R_{WS}} \times C_{WS} \times D, \quad (2)$$

where
$C_{WS}$ is the EPI concentration (mcg/mL) in the working standard solution on as is basis, $W_{WS}$ is the EPIB RS weight (mg) used to prepare the stock solution for working standard solution,
$V_{Stock}$ is the volume (mL) of the stock solution for working standard solution,
$V_1$ is the volume (mL) of the stock solution used for dilution in the working standard solution preparation,
$V_{WS}$ is the volume (mL) of the working standard solution,
$M_1$ is the molar mass of Epinephrine (183.20 g/mol),
$M_2$ is the molar mass of Epinephrine Bitartrate (333.29 g/mol),
P is the decimal purity factor on as is basis for the epinephrine bitartrate reference solution,
$R_{Smp}$ is the EPI peak area from the Sample Solution chromatogram and
$R_{WS}$ is the average peak area based on the five replicate injections of working standard solution.
D in Eq. 2 is a dilution factor, which is equal to unity for 8 mcg/mL products and to $V_{final}/V_{Smp}$ for products with other concentrations, where $V_{final}$ is the final volume of the diluted sample solution and $V_{Smp}$ is the volume of the sample solution used for dilution. D=2 and 4 for 16 mcg/mL and 32 mcg/mL sample solutions, respectively.

The assay result expressed as a percentage of the label claim for Epinephrine base (% LC) is calculated using Eq. 3.

$$\% \ LC = \frac{C_{Smp}}{LC} \times 100\%, \quad (3)$$

where
$C_{Smp}$ is the Sample Solution concentration (mcg/mL) calculated according to Eq. 2, LC is the product label claim expressed using the same concentration units, i.e. mcg/mL.

Determination of Related Compounds: Concentrations of individual impurities and degradants, $C_i$ (mcg/mL), in a Sample Solution are calculated using Eq. 4.

$$C_i = \frac{R_i}{R_{WS}} \times C_{WS} \times \frac{1}{RRF_i} \times D, \quad (4)$$

where,
$R_i$ is the peak area for i-th Impurity from the Sample Solution chromatogram,
$R_{WS}$ is the average peak area based on the 5 replicate injections of working standard solution and
$RRF_i$ is the relative response factor for i-th Impurity.
$C_{WS}$ and D are defined above.

The impurity content (% Imp) can also be expressed as a percent of the Label Claim (mcg/mL) for Epinephrine base:

$$\% \ Imp = \frac{C_i}{LC} \times 100\% \quad (5)$$

where,
$C_i$ is the concentration of individual impurities and degradants (mcg/mL), in the Sample Solution from Eq. 4 and LC is the product label claim expressed using the same concentration units, i.e. mcg/mL.

Table 17 depicts exemplary relative retention times and relative response factors for various impurities.

TABLE 17

| Compound | RRT | RRF |
|---|---|---|
| EPI (Epinephrine) | 1 | 1 |
| DHMA (DL-3,4-Dihydroxymandelic acid) | 0.58 | 1 |
| Imp B (Norepinephrine) | 0.69 | 1 |
| Imp C (Adrenalone) | 1.41 | 3.46 |
| Adrenochrome | 1.37 | 1.38 |
| MNE (Metanephrine) | 1.75 | 1 |
| NMD (N-Methyldopamine) | 1.67 | 1 |
| MOA (Methoxy Adrenaline) | 1.99 | 1 |
| NE-Imp E (Norepinephrine Impurity E (4-(Chloroacetyl)-catechol) | 3.55 | 1 |
| Imp E (2-(Benzylmethylamino)-3,4-dihydroxyphenyl)ethanone) | 4.08 | 1 |

Enantiomeric Purity of Epinephrine in Epinephrine Injection by HPLC-UV: In general, the determination of R- and S-enantiomers of EPI in the drug product solution is performed using an isocratic reverse-phase HPLC method with UV detection. Separation is achieved using a protein-based column with functional chiral selectors. The chiral selector is Cellobiohydrolase (CBH), which has been immobilized onto spherical silica particles. This enzyme preferentially separates compounds containing one or more basic nitrogen groups together with one or more hydrogen-accepting or hydrogen-donating groups. The active form of EPI is known to be the R-enantiomer (REPI). The S-enantiomer (SEPI), which may be present in the drug product, is quantitated as a percentage of the total response, i.e. by comparing the S-peak response to the sum of the R- and S-peak responses from a Sample solution chromatogram. The REPI and SEPI peaks are assigned by comparing their retention times in the Sample solution chromatogram to those in a standard solution chromatogram.

The HPLC system was equipped with a pump, a degasser, an autosampler, a thermostated column compartment and a PDA detector: Waters Alliance e2695 HPLC or equivalent. The chromatographic column was a Daicel Chiralpak CBH™ column, 5 μm, 4.0×100 mm, Sigma-Aldrich, C/N: 58550AST. Mobile Phase A was 10 mM Sodium Phosphate+EDTA buffer at pH 6.0, and Mobile Phase B was 100% isopropanol. Chromatographic conditions are shown in Table 18 below.

TABLE 18

| | |
|---|---|
| HPLC | Waters Alliance e2695 HPLC |
| Column | Daicel Chiralpak CBH ™ column, 5 μm, 4.0 × 100 mm |
| Column Temperature | 20° C. ± 2° C. |
| Sample Temperature | 5° C. ± 5° C. |
| Injection volume | 80 μL |
| Flow Rate | 0.7 mL/min |
| Detection | Single channel: 280 nm, resolution 6 nm<br>Spectrum: 200-600 nm, resolution 1.2 nm<br>Sampling Rate 5 points/s<br>Filter time Constant: Normal |
| Mobile Phase | MP A: 10 mM Sodium phosphate + EDTA buffer pH 6.0<br>MP B: 100% IPA |
| Gradient | Isocratic run (85% MP A:15% MP B) |
| Run Time | 10 min |

Determination of percentage of S-epinephrine: The percentage of SEPI, % S, in a Sample solution is calculated using Eq. 6.

$$\% S = \frac{A_{SEPI}}{A_{SEPI} + A_{REPI}} \times 100\%, \qquad (6)$$

where $A_{SEPI}$ is the SEPI peak area from the sample chromatogram, $A_{REPI}$ is the REPI peak area from the same sample chromatogram.

Therefore, various exemplary formulations of the inventive subject matter have been provided. The formulations of the inventive subject matter can be administered according to any suitable dosing schedule, which can vary depending on the condition to be treated.

The optimum therapeutically effective amount of a drug is the amount of the drug in the composition that will yield the most effective results in terms of efficacy of treatment in a given subject. This amount can vary depending upon a variety of factors, including but not limited to the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. The ready-to-administer formulations should also be able to pass readily through an injection device such as a hollow needle.

Depending on the particular purpose, it should also be recognized that contemplated compositions may be combined (in vivo, or in a therapeutic formulation or administration regimen) with at least one other therapeutically active agent to additively or synergistically provide a therapeutic or prophylactic effect.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. Moreover, where the term 'about' is used in conjunction with a numeral, a range of that numeral +/−10%, inclusive, is contemplated. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The discussion herein provides example epinephrine compositions and methods of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It should be apparent, however, to those skilled in the art that many more modifications besides those already described are possible without departing from the inventive concepts herein. The inventive subject matter, therefore, is not to be restricted except in the spirit of the disclosure. One skilled in the art will recognize many methods and materials similar or equivalent to those described herein, which could be used in the practice of the present invention. Indeed, the present invention is in no way limited to the methods and materials described.

Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. An antioxidant-free and storage stable ready-to-inject epinephrine composition, comprising:
   an aqueous pharmaceutically acceptable carrier containing epinephrine;
   wherein the epinephrine is present in the ready-to-inject epinephrine composition at a concentration of equal or less than 0.07 mg/ml;
   wherein substantially all of the epinephrine is an R-isomer;
   wherein the ready-to-inject epinephrine composition has a pH of between 3.0-4.7;
   wherein the ready-to-inject epinephrine composition further comprises a metal ion chelator present in the composition at a concentration of between about 1 and 50 ug/ml, wherein the metal ion chelator is selected from the group consisting of EDTA (edetic acid), EGTA, and diethylenetriaminepentaacetic acid; and
   wherein the ready-to-inject epinephrine composition has, after storage of at least one month, total impurities of equal or less than 0.7% and equal or less than 2% S-isomer content.

2. The composition of claim 1, wherein the epinephrine is present in the composition at a concentration of between about 0.005 mg/ml and 0.050 mg/ml.

3. The composition of claim 1, wherein the epinephrine is present in the composition at a concentration of between about 0.006-0.010 mg/ml.

4. The composition of claim 1, wherein the epinephrine is present in the composition at a concentration of between about 0.010-0.025 mg/ml.

5. The composition of claim 1, wherein the epinephrine is present in the composition at a concentration of between about 0.025-0.045 mg/ml.

6. The composition of claim 1, wherein the epinephrine is present in the composition as a pharmaceutically acceptable salt.

7. The composition of claim 1, wherein the ready-to-inject epinephrine composition has, after storage of at least one month, a pH of between about 3.5-4.5.

8. The composition of claim 1, wherein the ready-to-inject epinephrine composition has, after storage of at least one month, a pH of between about 3.8-4.2.

9. The composition of claim 1, wherein the aqueous pharmaceutically acceptable carrier is water for injection.

10. The composition of claim 1, wherein the aqueous pharmaceutically acceptable carrier further comprises a buffer.

11. The composition of claim 10, wherein the buffer is present in a concentration of between 1 mM and 25 mM, and wherein the buffer is selected from the group consisting of an acetate buffer, a citrate buffer, a phosphate buffer, a tartrate buffer, and a borate buffer.

12. The composition of claim 1, further comprising a tonicity agent selected from the group consisting of sodium chloride, glycerol, thioglycerol, mannitol, lactose, and dextrose.

13. The composition of claim 1, wherein the ready-to-inject epinephrine composition has dissolved oxygen of equal or less than 1.5 ppm $O_2$.

14. The composition of claim 1, wherein the ready-to-inject epinephrine composition has, after storage of at least one month, total impurities of equal or less than 0.5% and equal or less than 1% S-isomer content.

15. The composition of claim 1, wherein the ready-to-inject epinephrine composition has, after storage of at least one month, total impurities of equal or less than 0.2% and equal or less than 1.5% S-isomer content.

16. The composition of claim 1, wherein the ready-to-inject epinephrine composition has, after storage of at least one month, total impurities of equal or less than 0.5% and equal or less than 1% S-isomer content.

17. The composition of claim 1, wherein the ready-to-inject epinephrine composition has, after storage of at least one month, total impurities of equal or less than 0.3% and equal or less than 0.7% S-isomer content.

18. The composition of claim 1, wherein the ready-to-inject epinephrine composition has, after autoclaving, total impurities of equal or less than 0.5% and equal or less than 2.0% S-isomer content.

19. The composition of claim 1, wherein the ready-to-inject epinephrine composition has, after autoclaving, total impurities of equal or less than 0.2% and equal or less than 1.5% S-isomer content.

20. A pharmaceutical product, comprising:
a polymeric container comprising the antioxidant-free and storage stable ready-to-inject epinephrine composition of claim 1, wherein the container is a blow-fill-seal (BFS) container or flexible IV bag;
wherein the polymeric container has a volume of between 100 mL and 1,000 mL; and
wherein the polymeric container is optionally enclosed in a metallized over-container that optionally further comprises an oxygen scavenger or absorber disposed between the polymeric container and the metallized over-container.

* * * * *